US009228147B2

(12) United States Patent
Patil et al.

(10) Patent No.: US 9,228,147 B2
(45) Date of Patent: Jan. 5, 2016

(54) GLYCOL ETHER-BASED CYCLOHEXANOATE ESTERS, THEIR SYNTHESIS AND METHODS OF USE

(75) Inventors: Abhimanyu Onkar Patil, Westfield, NJ (US); Satish Bodige, Wayne, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 984 days.

(21) Appl. No.: 13/316,745

(22) Filed: Dec. 12, 2011

(65) Prior Publication Data

US 2012/0149620 A1 Jun. 14, 2012

Related U.S. Application Data

(60) Provisional application No. 61/422,886, filed on Dec. 14, 2010.

(51) Int. Cl.
*C10M 105/36* (2006.01)
*C08K 5/12* (2006.01)
*C10M 129/72* (2006.01)

(52) U.S. Cl.
CPC ........... *C10M 105/36* (2013.01); *C10M 129/72* (2013.01); *C08K 5/12* (2013.01); *C10M 2207/282* (2013.01); *C10M 2207/2825* (2013.01); *C10N 2230/02* (2013.01); *C10N 2230/06* (2013.01)

(58) Field of Classification Search
CPC ............. C10M 105/36; C10M 129/72; C10M 2207/282; C10M 2207/2825; C08K 5/12; C10N 2230/02; C10N 2230/06
USPC .......................................... 508/484; 560/426
See application file for complete search history.

(56) References Cited

U.S. PATENT DOCUMENTS

| | | | |
|---|---|---|---|
| 4,764,294 A | 8/1988 | Habeeb et al. | |
| 5,352,374 A | 10/1994 | Habeeb et al. | |
| 5,370,809 A | 12/1994 | Ishida et al. | |
| 5,512,189 A | 4/1996 | Wu et al. | |
| 5,531,911 A | 7/1996 | Adams et al. | |
| 5,631,212 A | 5/1997 | Vrahopoulou | |
| 6,165,949 A | 12/2000 | Berlowitz et al. | |
| 6,239,298 B1 | 5/2001 | Williamson et al. | |
| 6,355,186 B1 | 3/2002 | Shimomura et al. | |
| 6,824,671 B2 | 11/2004 | Goze et al. | |
| 7,754,663 B2 | 7/2010 | Habeeb et al. | |
| 2003/0130142 A1 | 7/2003 | Nguyen et al. | |
| 2004/0116643 A1 | 6/2004 | Kurihashi et al. | |
| 2005/0038283 A1 | 2/2005 | Kawahara et al. | |
| 2006/0183832 A1 | 8/2006 | Tsuchihashi et al. | |
| 2009/0281349 A1 | 11/2009 | Shieh et al. | |

FOREIGN PATENT DOCUMENTS

| | | | | |
|---|---|---|---|---|
| JP | 51-070396 | | 12/1974 | |
| JP | 52-121596 | | 3/1976 | |
| JP | 51070396 | * | 6/1976 | |
| JP | 60-181142 | | 2/1984 | |
| JP | 60181142 | * | 9/1985 | ............... C08K 5/11 |
| JP | 1999302445 | | 11/1999 | |
| JP | 2003268154 | | 9/2003 | |
| JP | 2008127342 | * | 6/2005 | ............... A61K 8/86 |
| JP | 2008-H66047 | | 6/2008 | |
| JP | 2008127342 | | 6/2008 | |
| JP | 2009035497 | | 2/2009 | |
| JP | 2009035498 | | 2/2009 | |
| JP | 2009057350 | | 3/2009 | |
| WO | 9213933 | | 8/1992 | |
| WO | WO0019972 | * | 4/2000 | ............... A61K 7/42 |

OTHER PUBLICATIONS

Translation of JP2008-127342, dated Jun. 5, 2008.*
Translation of JP60181142, dated Sep. 14, 1985.*
English translation of JP51070396, Jun. 17, 1976, pp. 1-15.*

* cited by examiner

*Primary Examiner* — Paul A Zucker
*Assistant Examiner* — Mark Luderer
(74) *Attorney, Agent, or Firm* — Robert A. Migliorini

(57) ABSTRACT

Glycol ether-based cyclohexanoate esters, their synthesis and methods of use as lubricant basestocks or co-basestocks.

18 Claims, No Drawings

US 9,228,147 B2

GLYCOL ETHER-BASED CYCLOHEXANOATE ESTERS, THEIR SYNTHESIS AND METHODS OF USE

CROSS-REFERENCE TO RELATED APPLICATIONS

This application claims priority to U.S. Provisional Application Ser. No. 61/422,886 filed Dec. 14, 2010, herein incorporated by reference in its entirety.

FIELD

This disclosure relates to novel glycol ether-based cyclohexanoate esters, their synthesis and methods of use as lubricant basestocks or co-basestocks.

BACKGROUND

The viscosity-temperature relationship of a lubricating oil is one of the critical criteria which must be considered when selecting a lubricant for a particular application. Viscosity Index (VI) is an empirical, unitless number which indicates the rate of change in the viscosity of an oil within a given temperature range. Fluids exhibiting a relatively large change in viscosity with temperature are said to have a low viscosity index. A low VI oil, for example, will thin out at elevated temperatures faster than a high VI oil. Usually, the high VI oil is more desirable because it has higher viscosity at higher temperature, which translates into better or thicker lubrication film and better protection of the contacting machine elements. In another aspect, as the oil operating temperature decreases, the viscosity of a high VI oil will not increase as much as the viscosity of a low VI oil. This is advantageous because the excessive high viscosity of the low VI oil will decrease the efficiency of the operating machine Thus high VI (HVI) oil has performance advantages in both high and low temperature operation. VI is determined according to ASTM method D 2270-93 [1998]. VI is related to kinematic viscosities measured at 40° C. and 100° C. using ASTM Method D 445-01.

In order to provide step-out fuel economy while maintaining or improving other lubricant performance features, basestocks with lower friction coefficients are needed. Low friction coefficients and low viscosities at all temperature ranges are two key properties contributing to lubricant fuel economy.

Synthetic lubricants having found increasing use as high performance basestocks. Because they are synthesized from relatively pure hydrocarbon components, synthetic lubricants tend to be more consistent in their compositions as compared to lubricant basestocks derived from crude oil refining processes. As such, their properties can be more readily controlled.

For example, polyalphaolefins (PAO) comprise a class of synthetic hydrocarbon lubricants, manufactured by the catalytic oligomerization (polymerization to low molecular weight products) of linear alpha-olefins (LAOS) typically ranging from 1-hexene to 1-octadecene, more typically from 1-octene to 1-dodecene, with 1-decene as the most common and often preferred material. Such fluids are described, for example, in U.S. Pat. No. 6,824,671 and patents referenced therein.

However, because PAOs are oligomerization/polymerization products, they exhibit distributions of molecular weights, which can negatively affect some aspects of their performance as lubricants. Likewise, in order to render PAOs suitable for use as lubricants, it is necessary to reduce the unsaturation of the as-polymerized carbon chains of the PAO products. Accordingly, it is conventional to hydrogenate these as-polymerized PAO products in order to reduce the level of unsaturation in the molecules, so as to render them suitable for use as lubricant basestocks, which is a costly process.

Another class of synthetic lubricant fluids useful as lubricant basestocks are polyalkylene glycols (PAG), which can often demonstrate improved friction coefficients, even as compared to PAO fluids. Some of these materials are described in the references set forth below.

Japanese Patent Application No. 51-070396 discloses lubricants containing a polyalkylene glycol ester with cyclohexanedicarboxylic acid which are heat resistant and useful for finishing undrawn nylon 6 or polyester fibers. The undrawn fibers were coated with an emulsion containing 10% of a composition of polyethylene glycol monolauryl ether 1,2-cyclohexanedicarboxylate, polyethylene glycol stearyl ether, polyethylene glycol castor oil ester and isohexadecyl phosphate Na salt, stored 24 hours at 20° and 65% relative humidity. No fume generation occurred on passing the resulting fibers over a plate at 180° and 100 m/min, whereas fume generation occurred on finishing the fibers with a comparative lubricant.

Japanese Patent Application No. 52-121596 discloses heat resistant lubricants for finishing of polyester fibers, which were prepared by blending a cyclohexanedicarboxylate or cyclohexenedicarboxylate of an alcohol containing alicyclic alkyl groups, optionally polyoxyalkylated, with a lubricant composition. The undrawn polyester fibers were coated with a 10% emulsion of a lubricant containing 70% diester of cyclohexanol-propylene oxide adduct with 1,2-chclohexanedicarboxylic acid to give drawn fibers without fume generation.

U.S. Pat. No. 5,370,809 discloses a synthetic lubricating oil comprising as a base oil at least one kind of carbonic acid ester represented by general formula (I):

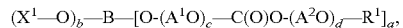

wherein $X^1$ is a member selected from the group consisting of a hydrogen atom, an alkyl group, a cycloalkyl group or a group having the formula $R^2$—$OA^3)_e$-, $A^1$, $A^2$ and $A^3$ are identical or different from each other and are each an alkylene group having 2-4 carbon atoms, $R^1$ and $R^2$ are identical or different from each other and are each a hydrogen atom, an alkyl group or a cycloalkyl group, B represents the residue of a compound having 3-20 hydroxyl groups, a is an integer of 1-20, b is an integer of 0-19, and the sum of a and b equals an integer of 3-20, c and d are each an integer of 0-50 with the proviso that c and d are not both zero and e is an integer of 1-50.

Japanese Patent Application No. 60-181142 discloses modified diesters of the formula $R(ZO)_mO_2Z^1CO_2(ZO)_nR$, wherein R=$C_{3-15}$ alkyl; Z=$C_{2-4}$ alkylene; $Z^1$=$C_{2-8}$ aliphatic or alicyclic dibasic acid residue; m, n=1,7; the sum of the number of C atoms in Z and R is 5-17, which show excellent plasticizing efficiency, migration and volatilization resistance, static charge dissipation and fogging resistance in chlorine-containing vinyl polymer compositions.

U.S. Pat. No. 6,239,298 discloses a fuel lubricity additive, made by a two-step process wherein the first step is co-reacting an unsaturated base oil, predominantly from vegetable oil sources, and a compound having a diene structure and a carboxylic acid group, wherein the second step is esterifying or amidifying the free carboxylic acid group of anhydride group with a poly-hydroxy-containing compound or polyamine compound to form the final fuel lubricity additive useful in diesel fuels. The inventive fuel lubricity additive also is useful as a dispersant.

U.S. Published Patent Application No. 2006/0183832 discloses a plasticizer for amorphous polyester resin which can give softness without hindering the transparency of the amorphous polyester resin, and an amorphous polyester resin composition superior in softness, transparency and heat resistance. A plasticizer for amorphous polyester resin, which is made of an ester of an (Aa) component selected from hydroxy aromatic carboxylic acid (AI), hydroxy condensed polycyclic aromatic carboxylic acid, hydroxy alicyclic carboxylic acid and others, and an (Ab) component selected from aliphatic alcohol, alicyclic alcohol, aromatic alcohol, phenol, alkylphenol, or alkylene oxide added products thereof.

However, PAG fluids, like PAOs, are also oligomer/polymer products of epoxides which have undesirable molecular weight distributions. Ethylene oxide or propylene oxide based PAG products are water soluble and hydrocarbon incompatible. Some of the detrimental aspects of PAG molecules includes oil miscibility (compatibility), elastomer compatibility and hygroscopicity.

There is a desire to have single molecule with precise structure for low viscosity basestocks. Thus, despite recent advances, there remains an unmet need in the art to develop synthetic materials suitable for use as a lubricant basestocks, which combine the advantages of both PAO and polyalkylene glycol fluids, but are discrete compounds having specific molecular weights.

SUMMARY

In a first embodiment, the present disclosure is directed to novel compounds of the general formula:

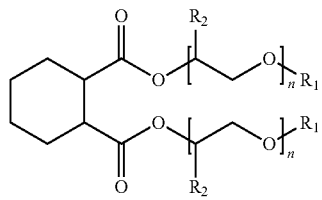

wherein $R_1$ is $C_1$ to $C_{12}$ linear or branched alkyl; $R_2$ is H or $CH_3$; n=2-4, and when n=4, $R_1$ is $C_2$ to $C_{12}$ linear or branched alkyl, which can find use as lubricant basestocks and/or co-basestocks.

An advantageous embodiment is directed to such compounds wherein $R_1$ is $C_2$ to $C_6$ alkyl.

Another advantageous embodiment is directed to such compounds wherein $R_1$ is $C_1$ to $C_6$ alkyl, $R_2$ is H, and n is 2 or 3.

In another advantageous embodiment the compounds are configured such that $R_1$ is $C_1$ to $C_6$ alkyl, $R_2$ is $CH_3$, and n is 2 or 3; or wherein $R_1$ is $C_2$ to $C_{12}$ alkyl, $R_2$ is H, and n is 4.

The following structures represent specific novel compounds which fall within the above general formula:

di(ethylene glycol)monohexyl cyclohexane-1,2-dicarboxylate of the structure:

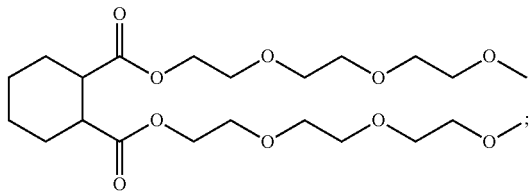

tri(ethylene glycol)monomethyl cyclohexane-1,2-dicarboxylate of the structure:

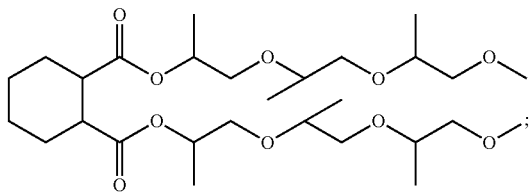

tri(propylene glycol)monomethyl cyclohexane-1,2-dicarboxylate of the structure:

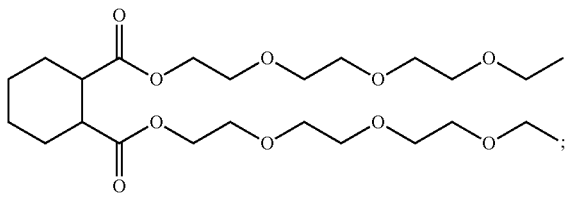

tri(ethylene glycol)monoethyl cyclohexane-1,2-dicarboxylate of the structure:

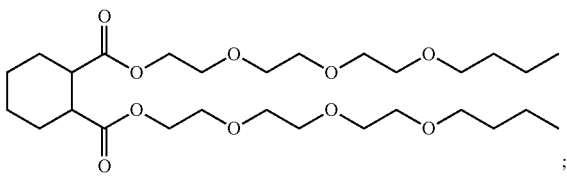 [SMILES: CCCCOCCOCCOCCOC(=O)C1CCCCC1C(=O)OCCOCCOCCOCCCC]

tri(ethylene glycol)monobutyl cyclohexane-1,2-dicarboxylate of the structure:

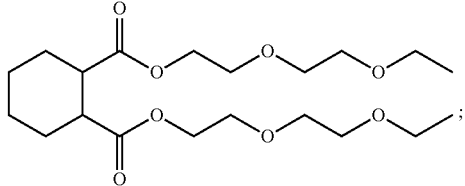 [SMILES: CCOCCOCCOC(=O)C1CCCCC1C(=O)OCCOCCOCC]

di(ethylene glycol)monoethyl cyclohexane-1,2-dicarboxylate of the structure:

di(ethylene glycol)monobutyl cyclohexane-1,2-dicarboxylate of the structure:

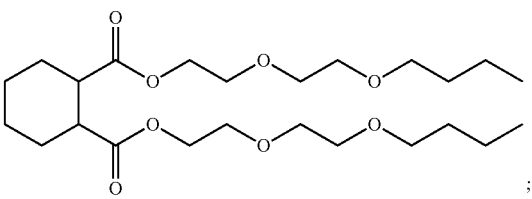 [SMILES: CCCCOCCOCCOC(=O)C1CCCCC1C(=O)OCCOCCOCCCC]

tri(propylene glycol)monopropyl cyclohexane-1,2-dicarboxylate of the structure:

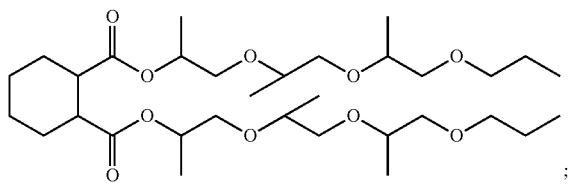 [SMILES: CCCOCC(C)OCC(C)OCC(C)OC(=O)C1CCCCC1C(=O)OC(C)COC(C)COC(C)COCCC]

tri(propylene glycol)monobutyl cyclohexane-1,2-dicarboxylate of the structure:

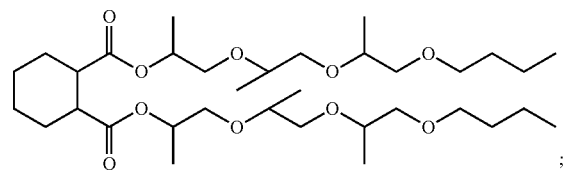 [SMILES: CCCCOCC(C)OCC(C)OCC(C)OC(=O)C1CCCCC1C(=O)OC(C)COC(C)COC(C)COCCCC]

and
poly(ethylene glycol)(4) dodecyl cyclohexane-1,2-dicarboxylate of the structure:

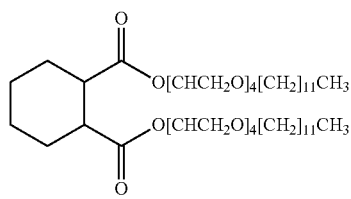

In another embodiment, the present disclosure is directed to a lubricant basestock or co-basestock comprising ethylene glycol mono-2-ethylhexyl cyclohexane-1,2-dicarboxylate of the structure:

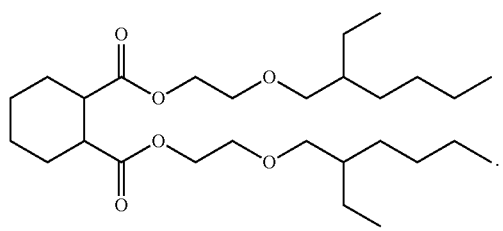 [SMILES: CCCCC(CC)COCCOC(=O)C1CCCCC1C(=O)OCCOCC(CC)CCCC]

Advantageously, when the compounds of the above formulae are co-basestocks, the basestock can be selected from the group consisting of a polyalphaolefin fluid, a metallocene-catalyzed polyalphaolefin fluid, a gas-to-liquid fluid and Group I to III basestocks.

DETAILED DESCRIPTION

All numerical values within the detailed description and the claims herein are modified by "about" or "approximately" the indicated value, and take into account experimental error and variations that would be expected by a person having ordinary skill in the art.

This disclosure is directed to a series of novel glycol ether-based cyclohexanoate ester fluids, their synthesis and methods of use. Ten new molecules were synthesized by the reaction of 1,2-cyclohexanedicarboxylic anhydride and glycol ethers. As an example, we have reacted 1,2-cyclohexanedicarboxylic anhydride with di(ethylene glycol)monohexyl ether to obtain a diester fluid represented by the following reaction mechanism:

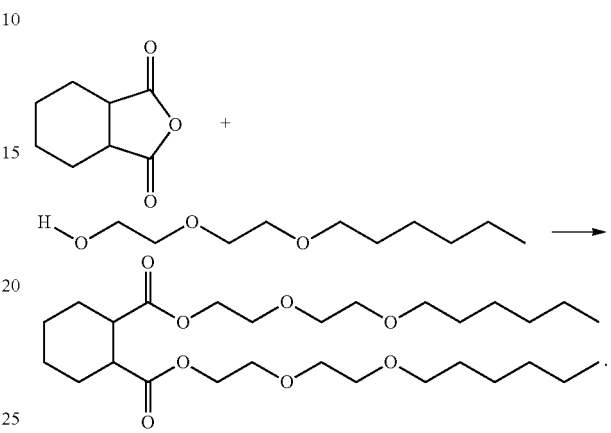

The novel glycol ether-based cyclohexanote esters are organic molecules with precise structures (not oligomers or polymers). These fluids are useful as low viscosity basestocks that contain both hydrocarbon and ether segments. We found that some of these molecules have poly-α-olefin (PAO)-like excellent lubricant properties, such as, high viscosity index (VI), and low pour point (PP). Additionally these molecules have lower friction coefficients compared to PAOs of similar viscosity, which should result in fuel economy advantages.

By changing the glycol ether portion, a series of molecules with varying polarity were synthesized. Similar types of products can also be prepared by reaction of glycol ethers with phthalic anhydride, or other aromatic or aliphatic acids. These novel molecules can be used as low viscosity basestocks or can be used as co-basestocks along with mPAO (metallocene PAO), PAO, Group I-III+, and GTL (gas-to-liquid) basestocks.

A wide range of lubricating base oils is known in the art. Lubricating base oils that are useful in the present disclosure are natural oils, synthetic oils, and unconventional oils. Natural oil, synthetic oils, and unconventional oils and mixtures thereof can be used unrefined, refined, or re-refined (the latter is also known as reclaimed or reprocessed oil). Unrefined oils are those obtained directly from a natural, synthetic or unconventional source and used without further purification. These include for example shale oil obtained directly from retorting operations, petroleum oil obtained directly from primary distillation, and ester oil obtained directly from an esterification process. Refined oils are similar to the oils discussed for unrefined oils except refined oils are subjected to one or more purification or transformation steps to improve at least one lubricating oil property. One skilled in the art is familiar with many purification or transformation processes. These processes include, for example, solvent extraction, secondary distillation, acid extraction, base extraction, filtration, percolation, hydrogenation, hydrorefining, and hydrofinishing. Re-refined oils are obtained by processes analogous to refined oils, but use an oil that has been previously used.

Natural oils include animal oils, vegetable oils (castor oil and lard oil, for example), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful in the present disclosure. Natural oils vary also as to the method used for their production and purification, for example, their distillation range and whether they are straight run or cracked, hydrorefined, or solvent extracted.

Groups I, II, III, IV and V are broad categories of base oil stocks developed and defined by the American Petroleum Institute (API Publication 1509; www.API.org) to create guidelines for lubricant base oils. Group I base stocks generally have a viscosity index of between 80 to 120 and contain greater than 0.03% sulfur and less than 90% saturates. Group II base stocks generally have a viscosity index of between 80 to 120, and contain less than or equal to 0.03% sulfur and greater than or equal to 90% saturates. Group III stock generally has a viscosity index greater than 120 and contains less than or equal to 0.03% sulfur and greater than 90% saturates. Group IV includes polyalphaolefins (PAO). Group V base stocks include base stocks not included in Groups I-IV.

Non-conventional or unconventional base stocks/base oils include one or more of a mixture of base stock(s) derived from one or more Gas-to-Liquids (GTL) materials, as well as isomerate/isodewaxate base stock(s) derived from natural wax or waxy feeds, mineral and or non-mineral oil waxy feed stocks such as slack waxes, natural waxes, and waxy stocks such as gas oils, waxy fuels hydrocracker bottoms, waxy raffinate, hydrocrackate, thermal crackates, or other mineral, mineral oil, or even non-petroleum oil derived waxy materials such as waxy materials received from coal liquefaction or shale oil, and mixtures of such base stocks.

GTL materials are materials that are derived via one or more synthesis, combination, transformation, rearrangement, and/or degradation/deconstructive processes from gaseous carbon-containing compounds, hydrogen-containing compounds, and/or elements as feedstocks such as hydrogen, carbon dioxide, carbon monoxide, water, methane, ethane, ethylene, acetylene, propane, propylene, propyne, butane, butylenes, and butynes. GTL base stocks and base oils are GTL materials of lubricating viscosity that are generally derived from hydrocarbons, for example waxy synthesized hydrocarbons, that are themselves derived from simpler gaseous carbon-containing compounds, hydrogen-containing compounds and/or elements as feedstocks. GTL base stock(s) include oils boiling in the lube oil boiling range separated/fractionated from GTL materials such as by, for example, distillation or thermal diffusion, and subsequently subjected to well-known catalytic or solvent dewaxing processes to produce lube oils of reduced/low pour point; wax isomerates, comprising, for example, hydroisomerized or isodewaxed synthesized hydrocarbons; hydroisomerized or isodewaxed Fischer-Tropsch (F-T) material (i.e., hydrocarbons, waxy hydrocarbons, waxes and possible analogous oxygenates); preferably hydroisomerized or isodewaxed F-T hydrocarbons or hydroisomerized or isodewaxed F-T waxes, hydroisomerized or isodewaxed synthesized waxes, or mixtures thereof.

A preferred fully formulated lubricant of the disclosure is prepared by blending or admixing with the base stock an additive package comprising but not limited to at least one of a detergent, and/or a dispersant, and/or an antioxidant, and/or a pour point depressant, and/or a VI improver, and/or antiwear agent, and/or extreme pressure additives, and/or a friction modifier, and/or a demulsifier, and/or an antifoamant, and/or antiseizure agent, and/or a corrosion inhibitor, and/or lubricity agent, and/or a seal swell control additive, and/or dye, and/or metal deactivators, and/or antistaining agent. Of these, those additives common to most formulated lubricating oils include a detergent, a dispersant, an antioxidant, an antiwear additive and a VI improver, with other additives being optional depending on the intended use of the oil. An effective amount of at least one or more additives, or an additive package is added to, blended into or admixed with the base stock to meet one or more formulated product specifications, such as those relating to a lube oil for diesel engines, internal combustion engines, automatic transmissions, turbine or jet, hydraulic oil, industrial oil, etc., as is known.

For a review of many commonly used additives see: Klamann in "Lubricants and Related Products" Verlog Chemie, Deerfield Beach, Fla.: ISBN 0-89573-177-0 which also has a good discussion of a number of the lubricant additives identified above. Reference is also made to "Lubricant Additives" by M. W. Ronney, published by Noyes Data Corporation, Parkridge, N.J. (1973). Various manufacturers sell such additive packages for adding to a base stock or to a blend of base stocks to form fully formulated lube oils for meeting performance specifications required for different applications or intended uses, and the exact identity of the various additives present in an additive pack is typically maintained as a trade secret by the manufacturer.

However, the chemical nature of the various additives is known to those skilled in the art. For example, alkali metal sulfonates, salicylates, and phenates are well known detergents which may be used, while PIBSA (polyisobutylene succinic anhydride) and PIBSA-PAM (polyisobutylene succinic anhydride amine) with or without being borated are well known and used dispersants. VI improvers and pour point depressants include acrylic polymers and copolymers such as polymethacrylates, polyalkylmethacrylates, as well as olefin copolymers, copolymers of vinyl acetate and ethylene, dialkyl fumarate and vinyl acetate, and others which are known. Friction modifiers include glycol esters and ether amines. Benzotriazole is a widely used corrosion inhibitor, while silicones are well known antifoamants. Antioxidants include hindered phenols and hindered aromatic amines such as 2,6-di-tert-butyl-4-n-butyl phenol and diphenyl amine, with copper compounds such as copper oleates and copper-PIBSA being well known. Antiwear additives include metal phosphate, metal dithiophosphate, metal dialkyl dithiophosphate, metal thiocarbamates, metal dithiocarbamates, metal dialkyl dithiocarbamates and ashless antiwear additives exemplified by ethoxylated amine dialkyldithiophosphates and ethoxylated amine dithiobenzoates as described in U.S. Pat. No. 6,165,949. Non-ionic ashless antiwear additives as described in U.S. Pat. No. 7,754,663, can also be used and they include thiosalicylic acid, organic group substituted thiosalicylic acid, organic esters of thiosalicylic acid, organic esters of organic group substituted thiosalicylic acid, thioromalonate, 2,2-dithiodipyridine, organic group substituted 2,2-dithiodipyridene, thiazolidine and organic group substituted thiazolidine.

This is meant to be an illustrative, but non-limiting list of the various additives used in lube oils. Thus, additive packages can and often do contain many different chemical types of additives. All of these additives are known and illustrative examples may be found, for example, in U.S. Pat. Nos. 5,352,374; 5,631,212; 4,764,294; 5,531,911 and 5,512,189.

EXAMPLES

Test Methods

The products were chemically characterized by various methods, including infrared spectroscopy (IR), GC-MS using standard 70 eV electron ionization (GC-EI-MS), NMR and electrospray ionization (ESI)/Fourier transform ion cyclotron resonance (FTICR) mass spectrometry.

Samples were prepared for electrospray ionization (ESI)/Fourier transform ion cyclotron resonance (FTICR) mass spectrometry and analyzed by the following process. The samples were diluted to 1 ppm in $MeOH/H_2O$ (9:1), and then analyzed with positive ion mode electrospray ionization (ESI) on an FTICR instrument (Bruker Daltonics Inc., Billerica, Mass., USA). Each of the mass spectra was obtained by summing up 24 scans. Cyclohexanoate esters were observed in the adduct form with either $Na^+$ or $NH_4^+$. Trace amount of $Na^+$ and $NH_4^+$ existing in the solvent or sample can be easily picked up during ESI ionization process. This is due to the nature of the ionization, not due to the sample. Exact mass measurement with FTICR determined the elemental composition.

Lube Properties and Friction Coefficient of Base Stock

The kinematic viscosity (Kv) of the liquid products was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. The friction coefficient of the products was measured using HFRR (high frequency reciprocating rig) test.

Example 1

Synthesis of di(ethylene glycol)monohexyl cyclohexane-1,2-dicarboxylate 1,2-cyclohexanedicarbocylic anhydride (50 g, 0.324 mol), di(ethylene glycol)monohexyl ether (135 g, 0.713 mol) and titanium tetra-isopropyl (1.47 g, 0.0052 mol) were mixed in 500 ml round bottom flask along with 170 ml xylene. The solution was refluxed for 18 h with a water condenser and a dean-stark trap. In 18 hours, 11 ml water was collected in the trap. Xylene was removed by simple distillation at 150° C. and excess di(ethylene glycol)monohexyl ether was distilled with an air bath oven at 185° C. under high vacuum. The product yield was 149 g (89%).

The product was characterized by IR, NMR and GCMS analysis. IR ($cm^{-1}$): 3451, 2931, 2859, 1737, 1454, 1376, 1332, 1302, 1246, 1176, 1126, 1045, 926, 880, 761, 726. NMR ($^{13}C$ δ ($CDCl_3$)): 173-175 (two $\underline{C}$=O), 71.5-70.1 (eight —O—$\underline{C}H_2$), 63.5 (two O=C—O—$\underline{C}H_2$), 44.7-42.5 (two —$\underline{C}H$—COO), 31.7 (two $CH_2$), 29.7-28.8 (two $CH_2$), 26.3 (two $CH_2$) 25.8-25.2 (two $CH_2$) 23.8 (two $CH_2$) 22.5 (two $CH_2$), 14.0 (two $CH_3$). NMR ($^1H$ δ ($CDCl_3$)): 0.88 (two $CH_3$, m), 1.2-2.1 (twelve —$CH_2$—, m), 2.85 (two CH, s), 3.4 (two —$CH_2O$—, t), 3.6-3.5 (two $OC\underline{H}_2$—$C\underline{H}_2O$—, m), 3.7 (two $OCH_2$—$C\underline{H}_2O$—, t), 4.3-4.1 (two O=C—$OCH_2$—, m).

The MS results confirmed the successful synthesis of the cyclohexanoate esters, as the molecular weights corresponding to the major peaks observed in mass spectrometer matched exactly with the expected molecular weights. The measured mass for the product was 539.3555 with assigned formula of $[C_{28}H_{52}O_8+Na]^+$ and calculated mass of 539.3554 with error (mDa) −0.1.

Example 2

Synthesis of tri(ethylene glycol)monomethyl cyclohexane-1,2-dicarboxylate 1,2-cyclohexanedicarboxylic anhydride (40 g, 0.260 mol), tri(ethylene glycol)monomethyl ether (94 g, 0.572 mol) and titanium tetra-isopropyl (1.2 g, 0.0042 mol) were mixed in 500 ml round bottom flask along with 200 ml xylene. The solution was refluxed for 18 h with a water condenser and a dean-stark trap. In 18 hours, 5 ml water was collected in the trap. Xylene was removed by simple distillation at 150° C. and excess tri(ethylene glycol)monomethyl ether was removed with an air bath oven at 185° C. under high vacuum. The product yield was 83 g (72%).

The product was characterized by IR, NMR and GCMS analysis. IR ($cm^{-1}$): 3452, 2926, 2870, 1726, 1740, 1452, 1351, 1302, 1247, 1197, 1124, 1043, 931, 852, 776. NMR ($^{13}C$ δ ($CDCl_3$)): 173-176 (two $\underline{C}$=O), 71.9-70.2 (four —O—$\underline{C}H_2CH_2$—O), 69.0 (two —O—$CH_2\underline{C}H_2$—O), 63.5 (two O=C—O—$\underline{C}H_2$), 58.8 (two O—$\underline{C}H_3$), 42.6-44.6 (two —$\underline{C}H$—COO), 28.9-23.6 (four $CH_2$). NMR ($^1H$ δ ($CDCl_3$)): 1.350-1.932 (four —$CH_2$—, s), 2.797 (CH, s), 3.32 (O—$CH_3$, s), 3.5 (—$CH_2O$—, m), 3.59 ($OCH_2$—$CH_2O$—, m), 4.16 (O=C—$OCH_2$—, m).

The sample was analyzed by GC-MS using standard 70 eV electron ionization (GC-EI-MS). The mass of the compound was found to be 462.2601, the calculated mass for $C_{22}H_{40}O_{10}$ was 464.2621, suggesting correct structure.

Example 3

Synthesis of tri(propylene glycol)monomethyl cyclohexane-1,2-dicarboxylate 1,2-cyclohexanedicarboxylic anhydride (40 g, 0.260 mol), tri(propylene glycol)monomethyl ether (84 g, 0.572 mol) and titanium tetra-isopropyl (1.2 g, 0.0042 mol) were mixed in 500 ml round bottom flask along with 150 ml xylene. Then solution was refluxed for 18 h with a water condenser and a dean-stark trap. In 18 hours, ~3 ml water was collected in the trap. Xylene was removed by simple distillation at 150° C. and excess tri(propylene glycol)monomethyl ether was removed with an air bath oven at 185° C. under high vacuum. The product yield was 111 g (99%).

The product was characterized by IR, NMR and MS analysis. IR ($cm^{-1}$): 2974, 2932, 1737, 1451, 1375, 1301, 1246, 1104, 1027, 967, 837, 757. NMR ($^{13}C$ δ ($CDCl_3$)): 172.9-177.3 (two C=O), 75.5 (two O—$CH_2$), 75.9-74.8 (four O—$\underline{C}H$), 73.4-73.0 (two O—$CH_2$), 71.8-71.2 (two O—$CH_2$), 70.0-69.4 (two O=C—O—$\underline{C}H$), 59.1-56.6 (two $OCH_3$), 44.7-42.5 (two —$\underline{C}H$—COO), 26.8-25.2 (two $CH_2$), 24.1-23.6 (two $CH_2$) 18.2-16.4 (six $CH_3$). NMR ($^1H$ δ ($CDCl_3$)): 1.3-1.1 (six $C\underline{H}_3$, m), 2.0-1.3 (four $C\underline{H}_2$), 3.0-2.5 (two CH—C=O, m) 3.4-3.2 (two $OCH_3$, s), 4.1-3.4 (six —$C\underline{H}_2O$; four —$C\underline{H}O$, m), 5.03 (two O=C—O—$C\underline{H}$, m).

The product was also characterized by electrospray ionization (ESI)/Fourier transform ion cyclotron resonance (FTICR) mass spectrometry. The MS results confirmed the successful synthesis of the cyclohexanoate esters, as the molecular weights corresponding to the major peaks observed in mass spectrometer matched exactly with the expected molecular weights. The measured mass for the product was 571.3455 with assigned formula of $[C_{28}H_{52}O_{10}+Na]^+$ and calculated mass of 539.3453 with error (mDa) −0.2.

Example 4

Synthesis of tri(ethylene glycol)monoethyl cyclohexane-1,2-dicarboxylate 1,2-cyclohexanedicarboxylic anhydride (25 g, 0.162 mol), tri(ethylene glycol)monoethyl ether (63 g, 0.572 mol) and titanium tetra-isopropyl (0.737 g, 0.0042 mol) were mixed in 500 ml round bottom flask along with 200 ml xylene. Then solution was refluxed for 18 h with a water condenser and a dean-stark trap. In 18 hours, 5-6 ml water was collected in the trap. Xylene was removed by simple distillation at 150° C. and excess tri(ethylene glycol)monomethyl ether was removed by washing with saturated $NaHCO_3$ and then distilled with an air bath oven at 185° C. under high vacuum. The product yield was 58 g (73%).

The product was characterized by IR, NMR and MS analysis. IR ($cm^{-1}$): 2863, 1452, 1349, 1301, 1113, 1045, 949, 865, 752. NMR ($^{13}C$ δ ($CDCl_3$)): 173-175 (two C=O), 71.9-69.6 (four —O—$CH_2CH_2$—O), 69.0 (two —O—$CH_2CH_2$—O), 66.5 (two $OCH_2$), 63.5 (two O=C—O—$CH_2$), 42.3-44.6 (two —CH—COO), 28.9-23.6 (four $CH_2$), 15.1 (two $CH_3$). NMR ($^1H$ δ ($CDCl_3$)): 1.2 (two $CH_3$, t), 1.3-2.0 (four —$CH_2$—), 2.8-2.6 (two CH, s), 3.7-3.3 (twelve —$CH_2O$—, m), 4.2 (two O=C—$OCH_2$—, m).

The product was also characterized by electrospray ionization (ESI)/Fourier transform ion cyclotron resonance (FTICR) mass spectrometry. Exact mass measurement with FTICR determined the elemental composition. The MS results confirmed the successful synthesis of the cyclohexanoate esters, as the molecular weights corresponding to the major peaks observed in mass spectrometer matched exactly with the expected molecular weights. The measured mass for the product was 515.2828 with assigned formula of $[C_{24}H_{44}O_{10}+Na]^+$ and calculated mass of 515.2827 with error (mDa) −0.1.

Example 5

Synthesis of tri(ethylene glycol)monobutyl cyclohexane-1,2-dicarboxylate 1,2-cyclohexanedicarboxylic anhydride (27 g, 0.175 mol), tri(ethylene glycol)monobutyl ether (85 g, 0.412 mol) and titanium tetra-isopropyl (0.830 g, 0.0028 mol) were mixed in 500 ml round bottom flask along with 150 ml xylene. Then solution was refluxed for 18 h with a water condenser and a Dean-Stark trap. In 18 hours, 6 ml water was collected in the trap. Xylene was removed by simple distillation at 150° C. and excess tri(ethylene glycol)monobutyl ether was removed by washing with saturated $NaHCO_3$ and then distilled with an air bath oven at 185° C. under high vacuum. The product yield was 79 g (82%).

The product was characterized by IR, NMR and MS analysis. IR ($cm^{-1}$): 2863, 1452, 1349, 1301, 1113, 1045, 949, 865, 752. NMR ($^{13}C$ δ ($CDCl_3$)): 173-175 (two C=O), 72.6-70.0 (ten —O—$CH_2CH_2$—O), 69.0 (two O—$CH_2$), 63.5 (two O=C—O—$CH_2$), 44.7-42.5 (two —CH—COO), 31.7 (two $CH_2$), 26.2-25.1 (two $CH_2$), 23.7 (two $CH_2$), 19.3 (two $CH_2$), 13.9 (two $CH_3$). NMR ($^1H$ δ ($CDCl_3$)): 0.9 (two $CH_3$, m) 1.2-2.1 (eight —$CH_2$—, m), 2.85 (two CH, s), 3.4 (two —$CH_2O$—, m), 3.7-3.4 (four $OCH_2$—$CH_2O$—, m; two O=C—$OCH_2$—$CH_2O$), 4.2 (two O=$COCH_2$, m).

The product was also characterized by electrospray ionization (ESI)/Fourier transform ion cyclotron resonance (FTICR) mass spectrometry. Exact mass measurement with FTICR determined the elemental composition. The MS results confirmed the successful synthesis of the cyclohexanoate esters, as the molecular weights corresponding to the major peaks observed in mass spectrometer matched exactly with the expected molecular weights. The measured mass for the product was 571.3460 with assigned formula of $[C_{28}H_{52}O_{10}+Na]^+$ and calculated mass of 571.3453 with error (mDa) −0.7.

Example 6

Synthesis of di(ethylene glycol)monoethyl cyclohexane-1,2-dicarboxylate 1,2-cyclohexanedicarboxylic anhydride (50 g, 0.324 mol), di(ethylene glycol)monoethyl ether (95.73 g, 0.7134 mol) and titanium tetra-isopropyl (1.47 g, 0.0052 mol) were mixed in 500 ml round bottom flask along with 170 ml xylene. Then solution was refluxed for 18 h with a water condenser and a Dean-Stark trap. In 18 hours, 11 ml water was collected in the trap. Xylene was removed by simple distillation at 150° C. and excess di(ethylene glycol)monoethyl ether was distilled with air bath oven at 185° C. under high vacuum. The product yield was 109 g (83%).

The product was characterized by IR, NMR and MS analysis. IR ($cm^{-1}$): 2864, 1735, 1452, 1375, 1350, 1302, 1247, 1176, 1116, 1046, 945, 865, 757. NMR ($^{13}C$ δ ($CDCl_3$)): 173-176 (two C=O), 70.5 (two $OCH_2$), 70.2-66.5 (six —O—$CH_2$—$CH_2$—O), 61.7 (two O=C—O—$CH_2$), 42.3-44.6 (two —CH—COO), 28.9-23.6 (four $CH_2$), 15.1 (two $CH_3$). NMR ($^1H$ δ ($CDCl_3$)): 1.2 (two $CH_3$, m), 1.3-2.0 (four —$CH_2$—, s), 2.8-2.6 (two CH, s), 3.7-3.3 (eight —$CH_2O$—, m), 4.2 (two O=C—$OCH_2$—, m).

The product was also characterized by electrospray ionization (ESI)/Fourier transform ion cyclotron resonance (FTICR) mass spectrometry. Exact mass measurement with FTICR determined the elemental composition. The MS results confirmed the successful synthesis of the cyclohexanoate esters, as the molecular weights corresponding to the major peaks observed in mass spectrometer matched exactly with the expected molecular weights. The measured mass for the product was 427.2303 with assigned formula of $[C_{20}H_{36}O_8+Na]^+$ and calculated mass of 427.2302 with error (mDa) −0.1.

Example 7

Synthesis of di(ethylene glycol)monobutyl cyclohexane-1,2-dicarboxylate 1,2-cyclohexanedixarboxylic anhydride (50 g, 0.324 mol), di(ethylene glycol)monobutyl ether (115 g, 0.713 mol) and titanium tetra-isopropyl (1.47 g, 0.0052 mol) were mixed in 500 ml round bottom flask along with 170 ml xylene. Then solution was refluxed for 18 h with a water condenser and a Dean-Stark trap. In 18 hours, 11 ml water was collected in the trap. Xylene was removed by simple distillation at 150° C. and excess di(ethylene glycol)monobutyl ether was distilled with an air bath oven at 185° C. under high vacuum. The product yield was 135 g (90%).

The product was characterized by IR, NMR and MS analysis. IR ($cm^{-1}$): 2956, 2861, 1735, 1453, 1352, 1302, 1247, 1176, 1115, 1046, 762. NMR ($^{13}C$ δ ($CDCl_3$)): 173-176 (two C=O), 71.1 (two $OCH_2$), 70.6-68.9 (six —O—$CH_2$—$CH_2$—O), 63.5 (two O=C—O—$CH_2$), 42.3-44.8 (two —CH—COO), 31.6 (two $CH_2$) 28.9-23.6 (four $CH_2$), 19.2 (two $CH_2$), 15.1 (two $CH_3$). NMR ($^1H$ δ ($CDCl_3$)): 0.9

(two CH$_3$, t), 1.3-2.0 (eight —CH$_2$—, m), 2.8-2.6 (two CH, s), 3.7-3.3 (eight —CH$_2$O—, m), 4.2 (two O=C—OCH$_2$—, m).

The product was also characterized by electrospray ionization (ESI)/Fourier transform ion cyclotron resonance (FTICR) mass spectrometry. Exact mass measurement with FTICR determined the elemental composition. The MS results confirmed the successful synthesis of the cyclohexanoate esters, as the molecular weights corresponding to the major peaks observed in mass spectrometer matched exactly with the expected molecular weights. The measured mass for the product was 483.2929 with assigned formula of $[C_{24}H_{44}O_8+Na]^+$ and calculated mass of 483.2928 with error (mDa) −0.1.

Example 8

Synthesis of tri(propylene glycol)monopropyl cyclohexane-1,2-dicarboxylate 1,2-cyclohexanedicarboxylic anhydride (25 g, 0.162 mol), tri(propylene glycol)monopropyl ether (62.8 g, 0.3567 mol) and titanium tetra-isopropyl (0.736 g, 0.0026 mol) were mixed in 500 ml round bottom flask along with 150 ml xylene. Then solution was refluxed for 18 h with a water condenser and a Dean-Stark trap. In 18 hours, 11 ml water was collected in the trap. The xylene was removed by simple distillation at 150° C. and excess of tri(propylene glycol)monopropyl ether was removed by washing with saturated NaHCO$_3$ and then distilled with an air bath oven at 185° C. under high vacuum. The product yield was 60 g (75%).

The product was characterized by IR, NMR and MS analysis. IR (cm$^{-1}$): 2933, 1732, 1454, 1375, 1300, 1110, 1027, 927, 838, 7672. NMR ($^{13}$C δ (CDCl$_3$)): 173.0-177.5 (two C=O), 75.9-74.9 four O—CH), 74.7-70.9 (eight O—CH$_2$), 70.0-69.0 (two O=C—O—CH), 44.7-42.5 (two —CH—COO), 26.8-24.2 (four CH$_2$), 24.1-23.6 (two CH$_2$), 18.5-16.4 (six CH$_3$), 10.6 (two CH$_3$). NMR ($^1$H δ (CDCl$_3$)): 0.9 (two CH$_3$), 1.3-1.1 (six CH$_3$, m), 2.0-1.3 (six CH$_2$, m), 3.0-2.5 (two CH—C=O, m), 4.1-3.1 (eight —CH$_2$O; four —CHO, m), 5.03 (two O=C—O—CH, m).

The product was also characterized by electrospray ionization (ESI)/Fourier transform ion cyclotron resonance (FTICR) mass spectrometry. Exact mass measurement with FTICR determined the elemental composition. The MS results confirmed the successful synthesis of the cyclohexanoate esters, as the molecular weights corresponding to the major peaks observed in mass spectrometer matched exactly with the expected molecular weights. The measured mass for the product was 627.4082 with assigned formula of $[C_{32}H_{60}O_{10}+Na]^+$ and calculated mass of 627.4079 with error (mDa) −0.3.

Example 9

Synthesis of tri(propylene glycol)monobutyl cyclohexane-1,2-dicarboxylate 1,2-cyclohexanedicarboxylic anhydride (25 g, 0.162 mol), tri (propylene glycol)monobutyl ether (67.77 g, 0.3567 mol) and titanium tetra-iso propyl (0.736 g, 0.0026 mol) were mixed in 500 ml round bottom flask along with 150 ml xylene. Then solution was refluxed for 18 h with a water condenser and a dean-stark trap. In 18 hours, ~5 ml water was collected in the trap. Xylene was removed by simple distillation at 150° C. and excess of tri(propylene glycol) monobutyl ether was removed with an air bath oven at 185° C. under high vacuum. The product yield was 86.25 g (84%).

The product was characterized by IR, NMR and MS analysis. IR (cm$^{-1}$): 2932, 2864, 1730, 1452, 1376, 1300, 1113, 1027, 837, 757. NMR ($^{13}$C δ (CDCl$_3$)): 173.0-177.5 (two C=O), 75.9-74.9 (four O—CH), 74.7-70.9 (eight O—CH$_2$), 70.0-69.0 (two O=C—O—CH), 44.7-42.5 (two —CH—COO), 32.3-31.5 (two CH$_2$), 26.8-23.8 (four CH$_2$), 19.3 (two CH$_2$) 19.1-16.4 (six CH$_3$), 13.9 (two CH$_3$). NMR ($^1$H δ (CDCl$_3$)): 0.9 (two CH$_3$, m), 1.3-1.1 (six CH$_3$, m), 2.0-1.3 (eight CH$_2$), 3.0-2.5 (two CH—C=O, m), 4.1-3.1 (eight, —CH$_2$O; four, —CHO, m), 5.03 (two O=C—O—CH, m).

The product was also characterized by electrospray ionization (ESI)/Fourier transform ion cyclotron resonance (FTICR) mass spectrometry. Exact mass measurement with FTICR determined the elemental composition. The MS results confirmed the successful synthesis of the cyclohexanoate esters, as the molecular weights corresponding to the major peaks observed in mass spectrometer matched exactly with the expected molecular weights. The measured mass for the product was 655.4395 with assigned formula of $[C_{34}H_{64}O_{10}+Na]^+$ and calculated mass of 655.4392 with error (mDa) −0.3.

Example 10

Synthesis of poly(ethylene glycol)(4) dodecyl cyclohexane-1,2-dicarboxylate 1,2-cyclohexanedicarboxylic anhydride (27 g, 0.1753 mol), poly (ethylene glycol) dodecyl ether (Brij 30) (140 g, 0.362 mol) and titanium tetra-iso propyl (0.816 g, 0.00287 mol) were mixed in 500 ml round bottom flask along with 200 ml xylene. Then solution was refluxed for 18 h with a water condenser and a Dean-Stark trap. In 18 hours, ~4 ml water was collected in the trap. The xylene was removed by simple distillation at 150° C. and excess of poly(ethylene glycol) dodecyl ether was removed with an air bath oven at 200° C. under high vacuum. The product yield was 147 g (98%).

The product was characterized by IR and NMR analysis. IR (cm$^{-1}$): 2924, 2854, 1736, 1455, 1350, 1302, 1251, 1173, 1115, 1046, 950, 865, 721. NMR ($^{13}$C δ (CDCl$_3$)): 173-175 (two C=O), 72.7-68.5 (six —O—CH$_2$CH$_2$—O; two —O—CH$_2$CH$_2$—O; two O—CH$_2$), 64.6-61.6 (two O=C—O—CH$_2$), 44.8-42.5 (two —CH—COO), 31.9 (two CH$_2$), 29.7-22.6 (twenty two CH$_2$), 14.1 (two CH$_3$). NMR ($^1$H δ (CDCl$_3$)): 0.9 (two CH$_3$, m), 1.2-2.1 (twenty —CH$_2$—, m), 2.1-1.5 (four CH$_2$), 2.9-2.6 (two CH, s), 3.4 (two —CH$_2$O—, t), 3.7-3.4 (six OCH$_2$—CH$_2$O—, m: two O=C—OCH$_2$—CH$_2$O), 4.2 (two O=COCH$_2$, m).

Example 11

Synthesis of ethylene glycol mono-2-ethylhexyl cyclohexane-1,2-dicarboxylate 1,2-cyclohexanedicarboxylic anhydride (50 g, 0.3243 mol), ethylene glycol mono-2-ethylhexyl ether (126 g, 0.7232 mol) and titanium tetra-isopropyl (1.49 g, 0.0052 mol) were mixed in 500 ml round bottom flask along with 200 ml xylene. Then solution was refluxed for 18 h with a water condenser and a Dean-Stark trap. In 18 hours, ~3 ml water was collected in the trap. Xylene was removed by simple distillation at 150° C. and excess ethylene glycol mono-2-ethylhexyl ether was removed with an air bath oven at 185° C. under high vacuum. The product yield was 156 g (99%).

The lube data was compared with PAO 4 (Table 1 below). Thus the viscometric data of the products suggests that the fluids have excellent lubricant properties that are comparable to PAO 4.

TABLE 1

| Sample # | $Kv_{100}$ | $Kv_{40}$ | Viscosity Index (VI) | Pour Point (° C.) | Friction Coefficient (FC) |
|---|---|---|---|---|---|
| Example 1 | 4.41 | 19.98 | 135 | −60.7 | 0.14 |
| Example 2 | 4.7 | 24.3 | 101 | −56 | 0.16 |
| Example 3 | 8.09 | 73.2 | 74 | −39 | 0.155 |
| Example 4 | 4.48 | 21.33 | 126 | −54 | 0.15 |
| Example 5 | 4.82 | 21.84 | 148 | −60 | 0.13 |
| Example 6 | 3.42 | 15.53 | 94 | −54 | 0.16 |
| Example 7 | 3.79 | 16.57 | 121 | −60 | 0.15 |
| Example 8 | 8.79 | 73.79 | 90 | −42 | 0.15 |
| Example 9 | 6.74 | 42.07 | 115 | −51 | 0.16 |
| Example 10 | 9.413 | 47.97 | 185 | −3 | — |
| Example 11 | 3.88 | 19.8 | 87 | — | — |
| PAO 4 | 4.1 | 19 | 126 | −66 | 0.21 |

Applicants have attempted to disclose all embodiments and applications of the disclosed subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All patents, test procedures, and other documents cited herein, including priority documents, are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

What is claimed is:

1. A lubricant comprising a basestock and/or a co-basestock of the formula:

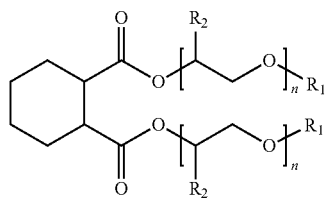

wherein $R_1$ is $C_1$ to $C_4$ linear or branched alkyl; $R_2$ is H or $CH_3$; and n=2-4.

2. The lubricant of claim 1, wherein $R_1$ is $C_2$ to $C_4$ alkyl.

3. The lubricant of claim 1, wherein $R_1$ is $C_1$ to $C_4$ alkyl, $R_2$ is H, and n is 2 or 3.

4. The lubricant of claim 1, wherein $R_1$ is $C_1$ to $C_4$ alkyl, $R_2$ is $CH_3$, and n is 2 or 3.

5. The lubricant of claim 1, wherein $R_1$ is $C_2$ to $C_4$ alkyl, $R_2$ is H, and n is 4.

6. A lubricant comprising a basestock and/or a co-basestock of the formula:

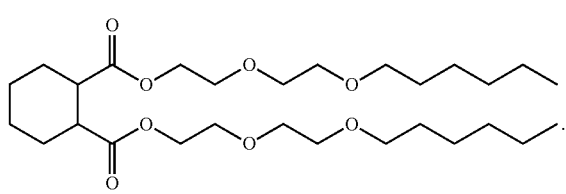 [SMILES: CCCCCCOCCOCCOC(=O)C1CCCCC1C(=O)OCCOCCOCCCCCC]

7. The lubricant of claim 1, wherein the basestock is of the formula:

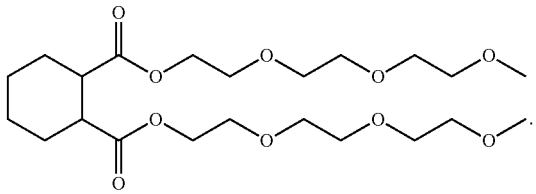 [SMILES: COCCOCCOCCOC(=O)C1CCCCC1C(=O)OCCOCCOCCOC]

8. The lubricant of claim 1, wherein the basestock is of the formula:

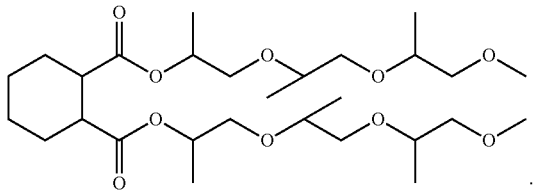 [SMILES: COCC(C)OCC(C)OCC(C)OC(=O)C1CCCCC1C(=O)OC(C)COC(C)COC(C)COC]

9. The lubricant of claim 1, wherein the basestock is of the formula:

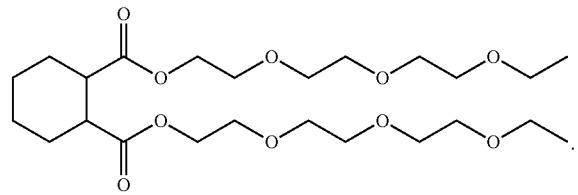 [SMILES: CCOCCOCCOCCOC(=O)C1CCCCC1C(=O)OCCOCCOCCOCC]

10. The lubricant of claim 1, wherein the basestock is of the formula:

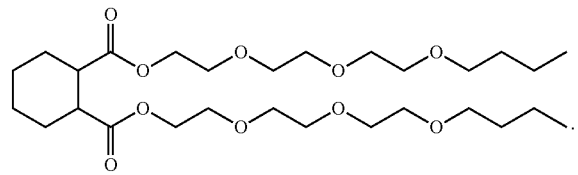 [SMILES: CCCCOCCOCCOCCOC(=O)C1CCCCC1C(=O)OCCOCCOCCOCCCC]

11. The lubricant of claim 1, wherein the basestock is of the formula:

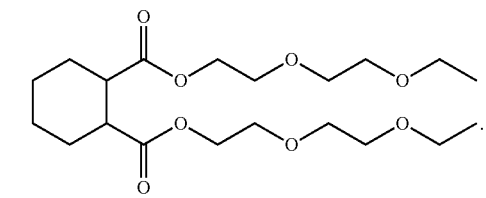 [SMILES: CCOCCOCCOC(=O)C1CCCCC1C(=O)OCCOCCOCC]

12. The lubricant of claim 1, wherein the basestock is of the formula:

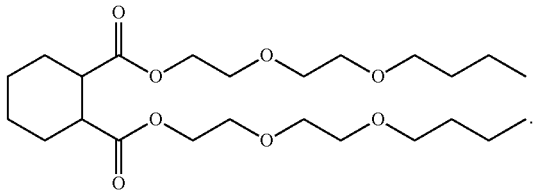 [SMILES: CCCCOCCOCCOC(=O)C1CCCCC1C(=O)OCCOCCOCCCC]

13. The lubricant of claim 1, wherein the basestock is of the formula:

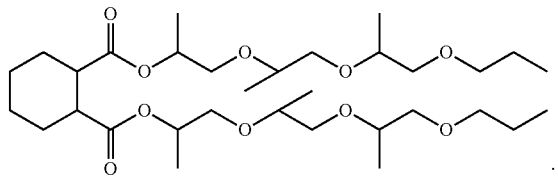 [SMILES: CCCOCC(C)OCC(C)OCC(C)OC(=O)C1CCCCC1C(=O)OC(C)COC(C)COC(C)COCCC]

14. The lubricant of claim 1, wherein the basestock is of the formula:

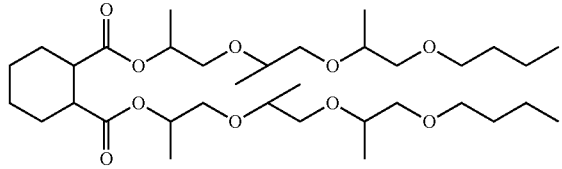

15. The lubricant of claim 1, further including a basestock or a co-basestock selected from the group consisting of a polyalphaolefin fluid, a metallocene-catalyzed polyalphaolefin fluid, a gas-to-liquid fluid and Group I to III basestocks.

16. A lubricant comprising a basestock and/or a co-basestock of the formula:

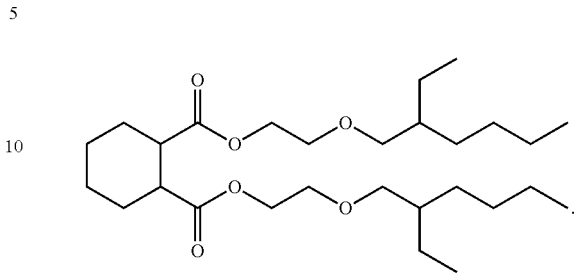

17. The lubricant of claim 16, further including a basestock or a co-basestock selected from the group consisting of a polyalphaolefin fluid, a metallocene-catalyzed polyalphaolefin fluid, a gas-to-liquid fluid and Group I to III basestocks.

18. The lubricant of claim 6, further including a basestock or a co-basestock selected from the group consisting of a polyalphaolefin fluid, a metallocene-catalyzed polyalphaolefin fluid, a gas-to-liquid fluid and Group I to III basestocks.

* * * * *